US009795468B2

(12) United States Patent
Mujwid et al.

(10) Patent No.: US 9,795,468 B2
(45) Date of Patent: Oct. 24, 2017

(54) IMPLANTS, TOOLS, AND METHODS FOR TREATMENT OF PELVIC CONDITIONS

(76) Inventors: James R. Mujwid, Edina, MN (US); John E. Titus, Lonsdale, MN (US)

( * ) Notice: Subject to any disclaimer, the term of this patent is extended or adjusted under 35 U.S.C. 154(b) by 499 days.

(21) Appl. No.: 14/008,208

(22) PCT Filed: Mar. 30, 2012

(86) PCT No.: PCT/US2012/031512
§ 371 (c)(1),
(2), (4) Date: Nov. 26, 2013

(87) PCT Pub. No.: WO2012/135652
PCT Pub. Date: Oct. 4, 2012

(65) Prior Publication Data
US 2014/0073847 A1    Mar. 13, 2014

Related U.S. Application Data

(60) Provisional application No. 61/469,473, filed on Mar. 30, 2011.

(51) Int. Cl.
*A61F 2/00*         (2006.01)

(52) U.S. Cl.
CPC .......... *A61F 2/0063* (2013.01); *A61F 2/0045* (2013.01); *A61F 2220/0016* (2013.01); *A61F 2250/0007* (2013.01); *A61F 2250/0018* (2013.01)

(58) Field of Classification Search
CPC ...................... A61F 2250/0007; A61F 2/0045
USPC .................................................... 600/29, 30
See application file for complete search history.

(56) References Cited

U.S. PATENT DOCUMENTS

| 3,885,570 | A | 5/1975 | Levine et al. |
| 6,911,002 | B2* | 6/2005 | Fierro ............... A61F 2/0045 |
| | | | 600/30 |
| 2002/0013982 | A1 | 2/2002 | Kipperman |
| 2005/0245946 | A1 | 11/2005 | Nash et al. |

(Continued)

FOREIGN PATENT DOCUMENTS

| EP | 2691046 B1 | 5/2016 |
| WO | 2010093421 A2 | 8/2010 |
| WO | 2012135652 A1 | 10/2012 |

OTHER PUBLICATIONS

First Examination Report for Australian Application No. 2016203700, dated Apr. 18, 2017, 4 pages.

(Continued)

*Primary Examiner* — Navin Natnithithadha
*Assistant Examiner* — Sunita Reddy
(74) *Attorney, Agent, or Firm* — Brake Hughes Bellermann LLP (57) ABSTRACT

Described are various embodiments of surgical procedures, systems, implants, devices, tools, and methods, useful for treating pelvic conditions in a male or female, the pelvic conditions including incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), and other conditions caused by muscle and ligament weakness, the devices and tools including devices and tools for anchoring an implant to supportive tissue and adjusting the implant.

16 Claims, 5 Drawing Sheets

(56) References Cited

U.S. PATENT DOCUMENTS

| | | | |
|---|---|---|---|
| 2006/0089525 A1* | 4/2006 | Mamo | A61B 17/0401 600/37 |
| 2006/0195011 A1* | 8/2006 | Arnal | A61B 17/06066 600/37 |
| 2006/0229596 A1* | 10/2006 | Weiser | A61B 17/00234 606/37 |
| 2007/0078295 A1* | 4/2007 | Landgrebe | A61B 17/0401 600/37 |
| 2009/0221868 A1* | 9/2009 | Evans | A61F 2/0045 600/37 |
| 2010/0113870 A1 | 5/2010 | Goldman | |
| 2010/0261950 A1 | 10/2010 | Lund et al. | |
| 2011/0004230 A1 | 1/2011 | Levine et al. | |
| 2014/0073847 A1 | 3/2014 | Mujwid et al. | |

OTHER PUBLICATIONS

Second Office Action for Canadian Application No. 2,839,851, dated Jan. 30, 2017, 7 pages.

\* cited by examiner

IMPLANTS, TOOLS, AND METHODS FOR TREATMENT OF PELVIC CONDITIONS

PRIORITY CLAIM

This application claims the benefit from International No. PCT/US2012/031512, which as granted an International Filing date of Mar. 30, 2012, which in turns claims priority under 35 USC §119(e) from U.S. Provisional Patent Application having Ser. No. 61/469,473 filed Mar. 30, 2011, which applications are incorporated herein by reference in their entireties.

FIELD OF THE INVENTION

The present invention relates generally to surgical methods and apparatus and, more specifically, to a surgically implantable sling having one or more adjustable features for treating incontinence or other pelvic disorders.

BACKGROUND

Pelvic health for men and women is a medical area of increasing importance, at least in part due to an aging population. Examples of common pelvic ailments include incontinence (e.g., fecal and urinary), pelvic tissue prolapse (e.g., female vaginal prolapse), and conditions of the pelvic floor.

Urinary incontinence can further be classified as including different types, such as stress urinary incontinence (SUI), urge urinary incontinence, mixed urinary incontinence, among others. Other pelvic floor disorders include cystocele, rectocele, enterocele, and prolapse such as anal, uterine and vaginal vault prolapse. A cystocele is a hernia of the bladder, usually into the vagina and introitus. Pelvic disorders such as these can result from weakness or damage to normal pelvic support systems.

Urinary incontinence can be characterized by the loss or diminution in the ability to maintain the urethral sphincter closed as the bladder fills with urine. Male or female stress urinary incontinence (SUI) generally occurs when the patient is physically stressed.

In its severest forms, vaginal vault prolapse can result in the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons. These procedures often involve lengthy surgical procedure times.

Urinary incontinence can be characterized by the loss or diminution in the ability to maintain the urethral sphincter closed as the bladder fills with urine. Male or female stress urinary incontinence (SUI) occurs when the patient is physically stressed.

The tension of an implant (i.e., "sling") is typically adjusted during an implantation procedure in a manner to take up slack in the sling and impart desirable and efficacious tension and positioning of the implanted sling and the supported tissue. New and improved methods of intra-operative implant adjusting mechanisms are always desirable. There is a desire to obtain a minimally invasive yet highly effective implantable mesh that can be used to treat incontinence (fecal or urinary), organ prolapse, and other pelvic conditions, with useful adjustability features.

SUMMARY

Devices, systems, and methods as described can be applied to treat pelvic conditions such as incontinence (various forms such as fecal incontinence, stress urinary incontinence, urge incontinence, mixed incontinence, etc.), vaginal prolapse (including various forms such as enterocele, cystocele, rectocele, apical or vault prolapse, uterine descent, etc.), levator defects, and other conditions caused by muscle and ligament weakness, hysterectomies, and the like.

Various surgical implants, tools, and methods that relate to useful or advantageous surgical procedures are described herein. Certain embodiments of method and implants involve an implant that includes an adjusting mechanism to adjust a length of an implant (e.g., a length of an extension portion or other portion or piece of an implant), intra-operatively.

Described devices and methods involve pelvic implants, including surgical implants (also referred to generally herein as "slings") that include a central support portion and two or more end portions extending from the central support portion to sling ends. Herein, the terms "sling," "implant," and "incontinence sling" without further qualification are used interchangeably to include various forms of pelvic implants for supporting different pelvic tissues, and specifically include urethral slings adapted to be placed through a tissue pathway in a male or female patient, disposing the central support portion below the urethra or bladder neck (hereafter collectively referred to as the urethra for convenience) (and above the vaginal wall in a female patient) to alleviate urinary incontinence, and fecal slings adapted to be placed through a tissue pathway disposing the central support portion inferior to the anus, the anal sphincter, or the lower rectum (hereafter collectively referred to as the anus for convenience) to alleviate fecal incontinence.

In accordance with the present description, such slings include features that enhance intra-operative adjustment of the tension applied to the urethra, anus, or other supported tissue, to enhance efficacy of the implant and method of treatment, and for improved patient comfort. Various specific embodiments of the implants and methods are described herein. The various embodiments are applicable to both male and female patients to address issues of incontinence in both, to address issues of prolapse repair in female patients, and to address perineal floor descent and fecal incontinence in both. Also, surgical techniques such as forming suprapubic, retropubic, transobturator, "inside-out," and "outside-in" tissue pathways between two skin incisions, or a tissue pathway formed from a single incision through the vagina or perineal floor (in male or female patients) are also contemplated for placement of a sling.

In various embodiments, sling tension or length of one or two extension portions of an implant can be adjusted by use of a line and a line holder that are located at a location of an implant that be accessed intra-operatively. Various line and line holder embodiments can be useful to decrease a length of an implant or extension portion, or optionally to increase an amount of tension in an implant or extension portion. Optionally, an implant or method can involve the use of a line at two opposing locations of an implant, each location being accessible through a surgical incision used to place an implant during a surgical implantation procedure. The two opposing adjusting mechanisms, each involving a line and a line holder, may be used in a coordinated manner, meaning that the tension or length of both of the two opposing extension portions are adjusted together. Such coordinated adjustment can advantageously allow a surgeon or other user to adjust the placement, length, or tension of an implant in a manner that does not cause a urethra or other tissue to become located at a non-anatomical position relative to a midline of the patient. Stated differently, two opposing extension portions of an implant can be adjusted together to prevent the urethra or other supported tissue from being moved in a left or a right direction within the patient, which will maintain a correct anatomical position of the urethra or other supported tissue, e.g., at a midline of the patient.

In one aspect the invention relates to a pelvic implant useful to treat a pelvic condition. The implant includes a tissue support portion, a first extension portion, and a second extension portion and a first adjusting mechanism that includes: a first line at the first extension portion, the first line being capable of being tightened to adjust a length of the first extension portion; and a first line holder that engages the first line and is capable of maintaining an adjusted length of the first extension portion. The implant includes a second adjusting mechanism that includes: a second line at the second extension portion, the second line being capable of being tightened to adjust a length of the second extension portion, and a second line holder that engages the second line and is capable of maintaining an adjusted length of the second extension portion. The implant optionally includes a self-fixating tip at the distal end of the first extension portion, and a self-fixating tip at the distal end of the second extension portion.

In another aspect, the invention relates to a method of treating a pelvic condition. The method includes providing an implant as described, placing the implant in a patient to support pelvic tissue, and actuating an adjusting mechanism to adjust a length of the extension portion.

DETAILED DESCRIPTION

Pelvic floor disorders include urinary and fecal incontinence, prolapse, cystocele, rectocele, enterocele, uterine and vaginal vault prolapse, levator defects, and others, in male and female patients. These disorders typically result from weakness or damage to normal pelvic support systems. Common etiologies include childbearing, removal of the uterus, connective tissue defects, prolonged heavy physical labor and postmenopausal atrophy.

Vaginal vault prolapse is the distension of the vaginal apex, in some cases to an orientation outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele, or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures for treating urinary incontinence include surgical methods that place a supportive implant such as a sling to stabilize or support the bladder neck or urethra. Various different supportive implants and sling procedures are known. Slings and methods can differ based on the type of sling material and anchoring methods used, and placement and technique for placing and supporting the sling, including tissue to be supported. In some cases, a sling is placed under the bladder neck and secured via suspension lines to a point of attachment (e.g. bone) through an abdominal or vaginal incision. Other techniques place a supportive portion of a sling below a urethra or bladder neck, and support the sling by placement of ends at or through obturator foramen tissue. Examples of sling procedures are disclosed in U.S. Pat. Nos. 5,112,344; 5,611,515; 5,842,478; 5,860,425; 5,899,909; 6,039,686, 6,042,534 and 6,110,101.

As used herein the terms "anchor," "tissue fastener," and "self-fixating tip," refer interchangeably and non-specifically to any structure that can connect an implant to supportive tissue of a pelvic region. The supportive tissue may preferably be a soft tissue such as a muscle, fascia, ligament, tendon, or the like. The anchor may be any known or future-developed structure useful to connect an implant to such tissue, including but not limited to a clamp, a line, a soft tissue anchor such as a self-fixating tip, and the like.

An implant can include a tissue support portion (or "support portion") that can be used to support a urethra (including a bladder neck), bladder, vagina, levator, rectum, sphincter, or other pelvic tissue. Supporting a "urethra" refers to supporting tissue that includes the urethra (which can refer to the bladder neck), and that can optionally include tissue adjacent to a urethra such as bulbospongiosus muscle, corpus spongiosum, or both. According to specific methods involving treatment of urinary incontinence, a support portion may be placed below bulbospongiosus muscle to support both bulbospongiosus muscle and corpus spongiosum (along with the urethra), or alternately bulbospongiosus muscle may be dissected and a support portion may be placed to contact corpus spongiosum tissue (to support the urethra).

An implant can additionally include one or more extension portion (otherwise known as an "end" portion or "arm") attached or attachable to the tissue support portion. Normally for treating incontinence an implant can include two opposing extension portions. Extension portions are elongate pieces of material (e.g., mesh, molded implant material, line, or biologic material) that extend from the tissue support portion and are connected to the tissue support portion, and are useful to attach to supportive tissue in the pelvic region (e.g., using an anchor such as a self-fixating tip or another form of tissue fastener) to thereby provide support for the tissue support portion and the supported tissue. Generally for treating incontinence, two extension portions can extend from opposite ends of a tissue support portion as elongate "ends," "arms," or "extensions," and may attach to supportive tissue in the pelvic region by extending through a tissue path to an internal anchoring point (see, e.g., Applicant's copending United States Patent Application Publication number US 2010/256442, filed Aug. 8, 2008, by Ogdahl, entitled SURGICAL ARTICLES AND METHODS FOR TREATING PELVIC CONDITIONS, the entirety of which is incorporated herein by reference), or may extend to an external incision, such as through an obturator foramen and through an external incision at a groin or inner thigh (see, e.g., Applicant's copending United States Patent Publication Number US 2006/0287571, the entirety of which is incorporated herein by reference). Also see U.S. Patent Publication number US 2011/0034759 and WO 2010/093421, PCT/US2010/057879, filed Nov. 23, 2010, and PCT/US2010/059739, filed Dec. 9, 2010, the entireties of which are incorporated hereby by reference.

In exemplary uses, each extension portion can extend from the location of attachment with the tissue support portion of the implant, through pelvic tissue, and to a location of supportive tissue within the pelvic region. The supportive tissue can be at an end of a tissue path used to perform a desired implant procedure, such as at a location at or near an end of an extension portion placed according to a single-incision placement procedure by way of a medial (e.g., vaginal or perineal) incision, specifically including tissue of an obturator foramen.

An implant may include portions, pieces, or sections that are synthetic or of biologic material (e.g., porcine, cadaveric, etc.). Extension portions may be, e.g., a synthetic mesh such as a polypropylene mesh, a molded implant material, or the like. The tissue support portion may be synthetic (e.g., a polypropylene mesh or a molded material) or biologic. Examples of implant products that may be similar to those useful according to the present description include those sold commercially by American Medical Systems, Inc., of Minnetonka Minn., under the trade names Apogee®, Perigee®, and Elevate® for use in treating pelvic prolapse (including vaginal vault prolapse, cystocele, enterocele, etc.), and Sparc®, Bioarc®, Monarc®, MiniArc®, InVance™, and AdVance™ for treating urinary incontinence.

An example of a particular type of pelvic implant is the type that includes supportive portions including or consisting of a tissue support portion and two extension portions extending from the tissue support portion. An implant that has exactly two extension portions can be of the type useful for treating urinary incontinence. The term "supportive portions" refers to portions of an implant that function to support tissue after the implant has been implanted and specifically includes extension portions, tissue support portions, and an adjusting mechanism (e.g., line) as described herein, and does not include optional or appurtenant features of an implant such as a tissue fastener, self-fixating tip, or other type of connector for attaching the implant to an insertion tool or supportive tissue.

Dimensions of a tissue support portion can be any dimensions useful to support a specific tissue, e.g., urethral or vaginal tissue, for treating a pelvic condition such as incontinence, prolapse, or another pelvic condition. A tissue support portion for use in treating incontinence can be of sufficient length to support and optionally partially surround a urethra or urethra-supporting tissue. A width of a tissue support portion may optionally and preferably be greater than a width of extension portions and can be sufficiently wide to increase contact area and frictional forces between a tissue support portion and a tissue in contact with the tissue support portion. Exemplary lengths of a tissue support portion can be in the range from 0.5 to 2 inches, such as from 0.75 to 1.5 inches. Exemplary widths of a tissue support portion can be in the range from 0.4 or 0.5 to 4 centimeters, such as from 1 to 2.5 or 3 centimeters.

An implant (e.g., sling) for placement against a corpus spongiosum for treatment of urinary incontinence in a male patient may optionally and preferably include a widened central support to provide increased contact and frictional engagement with the corpus spongiosum. See, for example, Assignee's copending United States Patent Publication Number US 2006/0287571 and U.S. Pat. No. 7,422,557, the entireties of these applications being incorporated herein by reference.

Dimensions of extension portions can allow the extension portion to reach between a tissue support portion placed to support a pelvic tissue such as tissue of a urethra, (at an end of the extension portion connected to the tissue support portion) and a location at which the distal end of the extension portion attaches to supportive tissue at or about the pelvic region, such as an obturator foramen. Exemplary lengths of an extension portion for use in treating incontinence by placing ends of an extension portion at tissue of an obturator foramen, for example, measured between a connection or boundary between the extension portion and the tissue support portion and a distal end of the extension portion, can be, e.g., from 0.5 to 2.5 inches, preferably from 0.5 to 1.5 inches. These or other lengths will be useful for implants designed to treat other conditions.

Implants as described can include a tissue fastener at a distal end or a distal portion of an extension portion, which is the end or portion not attached to a tissue support portion. (The term "distal" as used in this context generally refers to location at an end of an extension portion away from a tissue support portion.) A tissue fastener at a distal end of an extension portion can be any of various types, including: a self-fixating tip that is inserted into soft tissue and frictionally retained; soft tissue anchors; biologic adhesive; a soft tissue clamp that can generally include opposing, optionally biased, jaws that close to grab tissue; and opposing male and female connector elements that engage to secure an end of an extension portion to tissue. (See International Patent Publication No. WO2011/063412, entitled "Surgical Implants, Tools, and Methods for Treating Pelvic Conditions, filed Jun. 15, 2007; U.S. patent application Ser. No. 12/223,846, filed Aug. 8, 2008, entitled SURGICAL ARTICLES AND METHODS FOR TREATING PELVIC CONDITIONS, now U.S. Pat. No. 9,144,426; U.S. patent application Ser. No. 12/669,099, filed Jan. 14, 2010, entitled PELVIC FLOOR TREATMENTS AND RELATED TOOLS AND IMPLANTS, now U.S. Pat. No. 8,597,173; and WO 2009/075800, the entireties of which are incorporated herein by reference.)

One embodiment of a tissue fastener is a self-fixating tip. A "self-fixating tip" in general can be a structure (sometimes referred to as a soft tissue anchor) connected at a distal end of an extension portion that can be implanted into supportive tissue (e.g., muscle, fascia, ligament, or other soft tissue) in a manner that will maintain the position of the self-fixating tip and support the attached implant. Exemplary self-fixating tips can also be designed to engage an end of an insertion tool (e.g., elongate needle, elongate tube, etc.) so the insertion tool can be used to push the self-fixating tip through and into tissue for implantation, preferably also through a medial incision to reach the interior of the pelvic region, e.g., at a location of an obturator foramen or other supportive tissue. The insertion tool may engage the self-fixating tip at an internal channel of the self-fixating tip, at an external location such as at an external surface of the base, at a lateral extension, or otherwise as desired, e.g., in a manner to allow the insertion tool to push the self-fixating tip through an incision in a patient and through and into supportive tissue.

Exemplary self-fixating tips can include one or more lateral extensions that allow the self-fixating tip to be inserted into soft tissue and to become effectively anchored in supportive tissue. A lateral extension may be moveable or fixed. The size of the self-fixating tip and optional lateral extensions can be useful to penetrate and become anchored into the tissue. Exemplary self-fixating tips are described in Assignee's copending international patent application PCTUS2007/004015, filed Feb. 16, 2007, titled Surgical Articles and Methods for Treating Pelvic Conditions, the entirety of which is incorporated herein by reference. Other structures may also be useful.

According to exemplary embodiments, a self-fixating tip can have structure that includes a base having a proximal base end and a distal base end. The proximal base end can be connected (directly or indirectly, such as by a connective line) to a distal end of an extension portion. The base extends from the proximal base end to the distal base end and can optionally include an internal channel extending from the proximal base end at least partially along a length of the base toward the distal base end. The optional internal channel can be designed to interact with (i.e., engage, optionally by means of a release mechanism that can be selectively engaged and released) a distal end of an insertion tool to allow the insertion tool to be used to place the self-fixating tip at a location within pelvic tissue of the patient. A self-fixating tip can be made out of any useful material, generally including materials that can be molded or formed to a desired structure and connected to or attached to a distal end of an extension portion of an implant. Useful materials can include plastics such as polyethylene, polypropylene, and other thermoplastic or thermoformable materials, as well as metals, ceramics, and other types of biocompatible and optionally bioabsorbable or bioresorbable materials. Exemplary bioabsorbable materials include, e.g., polyglycolic acid (PGA), polylactide (PLA), copolymers of PGA and PLA.

According to various systems as described, one or more instrument, insertion tool, adjusting tool, or the like, may be incorporated or used with an implant or method as described. Examples of useful tools include those that generally include one or more (stationary or moveable) thin elongate, relatively rigid shaft or needle that extends from a handle. The handle is located at a proximal end of the device and attaches to one end (a proximal end) of a shaft.

According to some embodiments, a distal end of a shaft can be adapted to engage a portion of an implant such as a tissue fastener (e.g., a self-fixating tip), in a manner that allows the insertion tool to engage and push the tissue fastener through a tissue passage and connect the tissue fastener to supportive tissue of the pelvic region. Examples of this type of tool can be used with a self-fixating tip that includes an internal channel designed to be engaged by a distal end of an insertion tool to allow the self-fixating tip to be pushed into tissue. Other general types of insertion tools will also be useful, but may engage a self-fixating tip or other tissue fastener in an alternate manner, e.g., that does not involve an internal channel.

Exemplary insertion tools for treatment of incontinence and vaginal prolapse are described, e.g., in U.S. patent application Ser. No. 10/834,943, now U.S. Pat. No. 7,500,945, Ser. No. 10/306,179, now U.S. Pat. No. 7,070,556; Ser. No. 11/347,553, now U.S. Pat. No. 7,422,557; Ser. No. 11/398,368, now U.S. Pat. No. 7,740,576; Ser. No. 10/840,646 now U.S. Pat. No. 7,351,197; PCT application number 2006/028828, now U.S. Pat. No. 8,535,217; United States Patent Publication Number 2006/0260618; WO 2010/093421, and US Patent Publication No. 2010-0256442 the entireties of these documents being incorporated herein by reference. These and similar tools can be used as presented in the referenced documents, or with modifications to provide features identified in the present description.

An insertion tool can optionally include a mechanism (a "release mechanism") by which a tissue fastener (e.g., a self-fixating tip) can be securely and releasable engaged with a distal end of an insertion tool such that the tissue fastener can be selectively secured to the distal end mechanically, then selectively released. With a releasable engagement, a tissue fastener (e.g., self-fixating tip) can be released from the distal end by releasing the engagement (e.g., mechanical engagement) by movement of an actuator at the proximal end of the insertion tool, such as at the handle. For example, an internal channel (or external surface) of a self-fixating tip can include an engaging surface designed to engage a mechanism at a distal end of an insertion tool shaft, while the self-fixating tip is placed at, on, or over the distal end. As an example, an internal or external surface of a self-fixating tip can include a depression, ring, edge, or ledge, that can be rounded, angular, etc. A mechanical detent such as a pin, ball, spring, lever, deflector, or other surface or extension located at the distal end of the insertion tool can be moved, deflected, or extended relative to the distal end of the insertion tool to contact the surface of the self-fixating tip to securely and releasably hold the self-fixating tip at the distal end of the insertion tool and selectively prevent removal of the tip from the distal end until removal is desired. The detent (or other surface or mechanism) can be caused to extend (or retract) from the distal end of the insertion tool by actuating a trigger or other mechanism located at the proximal end (e.g., handle or a proximal location of a shaft) of the insertion tool, to secure (or release) the self-fixating tip. Upon placement of the self-fixating tip at a desired location during a surgical implantation procedure, the insertion tool operator can release the self-fixating tip by use of the trigger or other mechanism at the handle to disengage the detent and cause the tip to become loose. The insertion tool can then be removed from the tissue path and the self-fixating tip can remain in a desired implanted location.

One exemplary form of implant useful for treatment of urinary incontinence is a "mini-sling," or "single incision sling," (e.g., as marketed by American Medical Systems under the trade name MINIARC™). These devices and methods can be suitable for treating male or female urinary and incontinence by placement of the sling in a therapeutic anatomical location below a patient's urethra, through a single vaginal or perineal incision, with placement of tissue fasteners at opposing obturator foramen.

An implant as described herein can include one or preferably two adjusting mechanisms, each including a line and a line holder. The implant may optionally and preferably (but not necessarily) be formed into three separate pieces of mesh or molded implant material: a center piece or "tissue support portion piece" that includes the tissue support portion and two opposing ends; a first extension portion piece that that includes a proximal end and a distal end, the distal end optionally and preferably including a self-fixating tip; and a second extension portion piece that includes a proximal end and a distal end, the distal end optionally and preferably including a self-fixating tip. According to these multi-piece (e.g., three-piece) embodiments, a first adjusting mechanism that includes a line and a line holder adjustably connects the proximal end of the first extension portion piece to one end of the tissue support portion piece. A second adjusting mechanism that includes a second line and a second line holder adjustably connects the proximal end of the second extension portion piece to the other end of the tissue support portion piece.

A "line" as a component of an adjusting mechanism can be extended between a proximal end of an extension portion piece and an end of a tissue support portion piece in a manner that allows one end or segment of the line to be directly or indirectly pulled, e.g., proximally, to adjust a length of an extension portion of an implant, to consequently achieve a desired tension of the implant and a desired placement of supported tissue. As used herein, a "line" is a relatively flexible elongate body made of any material, such as polymer, natural or synthetic fiber, metal, etc., that may be braided, extruded, twisted, molded, knitted, or otherwise formed, and that can be extended between locations of an implant to adjust (especially reduce) a desired dimension (e.g., length) of an implant or an extension portion. Examples of structures useful as a "line" include any elongate structure in the form of a strand, surgical suture, thread, filament, cord, cable, lead, wire, string, twine, monofilament, flat or circular cross-sectional polymeric strip, flexible elongate tube, as well as any other circular, flat, or non-circular cross sectional structure that can function as a line as described herein.

In certain embodiments, a line can be used to directly affect a length of an extension portion, such as by reducing a distance between an extension portion piece and a support portion piece of the implant. The line can be securely connected to an end of the extension portion piece, an end of the support portion piece, or both. Alternately or in addition, the line may be loosely threaded through an end of the extension portion piece, an end of the support portion piece, or both. In use, the line may be pulled, directly or indirectly through another structure such as a tether or a line holder, e.g., proximally, to reduce a distance between the extension portion piece and the support portion piece.

An adjusting mechanism can also include at least one tether that extends between the implant and a proximal location. The tether may be the line, a direct or indirect connection of the line, or otherwise connected directly or indirectly (e.g., through a line holder) to the line, in a manner that places traction on the tether, such as by pulling in a proximal direction, places traction on the line. For example, traction on the tether can place traction on the line to pull an end or segment of the line in a direction to reduce a length of an extension portion. A preferred tether can include a loose tether end that can be located a distance away from the implant to allow the loose tether end to be manipulated intra-operatively, during a surgical procedure, through a medial incision. With the implant placed to support a pelvic tissue and with two tissue fasteners placed at supportive tissue such as at opposing obturator foramen, the tether can be pulled (e.g., proximally) to manually actuate the adjusting mechanism, or to actuate the adjusting mechanism without the need for a specialized tool to directly engage the adjusting mechanism intra-operatively. Preferably a loose tether end can be of a length sufficient to allow the loose tether end to extend to or close to an exterior location, through a medial incision, with the implant placed to support a pelvic tissue and with two tissue fasteners placed at supportive tissue such as at opposing obturator foramen.

The line works in conjunction with a line holder, which can be connected to the line at one or more locations, and that can move along a length of the line. The line holder can be connected to or engaged with the line in a manner that allows the line to move relative to (e.g., through, around, within, alongside, or the like) the line holder to allow the line holder to selectively secure a length of the line (or a segment thereof) between pieces of an implant to maintain a length of an extension portion. In use, the line can be pulled (optionally released) in a manner to adjust the tension placed by the tissue support portion piece on supported tissue (e.g., a urethra), by affecting a length of an extension portion. When desired length and tension of the implant, and placement of the supported tissue, are achieved, the line holder can secure the achieved length, tension, and position, to hold the length, tension, and position post-operatively.

The line holder can be any type of mechanical fixture that can engage a line to allow movement of a segment of the line during adjustment, and be secured to the line to secure a length of the line as that length defines a length of an extension portion. A line may be passed through or threaded through a line holder, or adjacent to the line holder, or about or around the line holder, to allow the line and the line holder to move relative to each other. The line holder can be selectively fixed to the line (or the line and a component of the implant) in a manner to hold a desired length of the line to maintain desired tension in the implant and position of supported pelvic tissue (e.g., urethra). Once fixed, the length of the extension portion is set to not increase, but to hold supported pelvic tissue in place at the supported position and not release substantially, even gradually during a post-operative healing or in-growth period (e.g., up to three weeks).

Examples of line holders include rigid non-deformable, or deformable semi-rigid or elastic devices of any structure that can be used to frictionally prevent a line, once held, from moving relative to implant pieces in a manner that would increase a length of an extension portion, e.g., increase a distance between a tissue support portion piece and an extension portion piece. A useful line holder may be a cam, bracelet, clip, body with apertures, plug, etc., having a moveable or fixed (relative to the line holder) frictional surface that engages a line to prevent movement at least in a direction that would increase a length of an extension portion. Examples of useful line holders include simple frictional structures such as a biased (e.g., spring-loaded) lever or detent that can frictionally and selectively engage or disengage a line. Others useful line holders include solid bodies that may non-rigid, deformable, or compressible bodies that, especially when engaging a line that is under tension, can engage the line with deformation of the line, the line holder, or both, to frictionally prevent movement of the line relative to the line holder. Certain useful line holders can selectively deform the line to prevent the line from passing through a structure (e.g., aperture) of a piece of an implant; with the implant under tension, the optionally deformed line holder and optionally deformed line are of a dimension that prevents their passage through the aperture, thus preventing a length of the implant (e.g., extension portion) from increasing.

Figure 1:
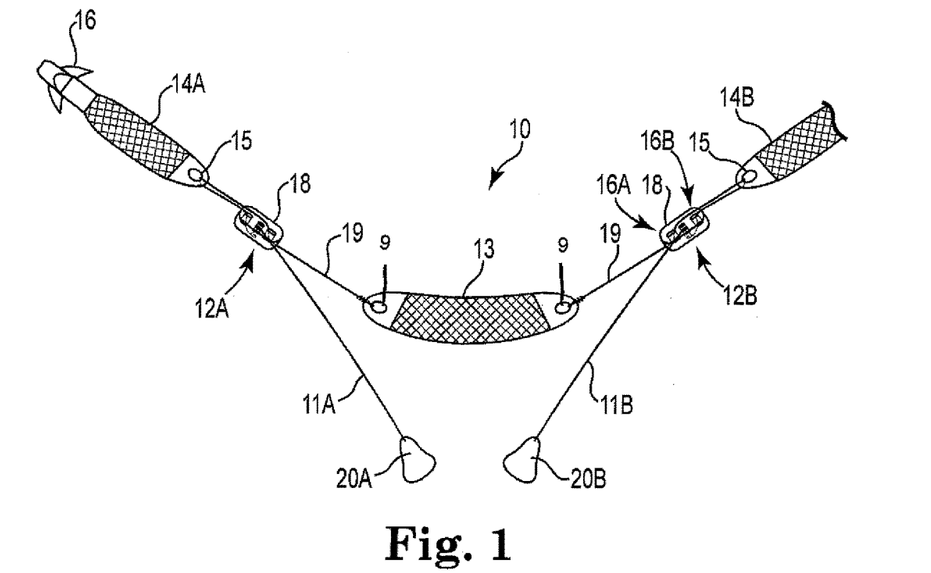
FIG. 1 shows an embodiment of an implant as described.

Referring to FIG. 1, an exemplary embodiment of an elongated sling 10 is shown in which features of the present description, including adjusting mechanisms including a line and a line holder, are included. Sling 10 includes three implant pieces (e.g., of mesh or molded materials): extension portion piece 14A, extension portion piece 14B, and tissue support portion piece 13. Implant 10 may be implanted by use of any useful method and pathways through which at least extension portions of sling 10 are drawn to dispose support portion piece 13 in operative relation to supported pelvic tissue, such as a urethra or bladder neck (or other pelvic tissue such as an anal sphincter). Sling 10 includes two opposing extension portions (which include but are not necessarily defined by or co-extensive with an extension portion piece 14A, 14B), one or more optional tissue fastener 16 located at one or more distal end of the extension portions, and a tissue support portion that is part of (but not necessarily co-extensive with) tissue support portion piece 13. Two adjusting mechanisms 12A and 12B are located on two opposing sides of tissue support portion piece 13. Each adjusting mechanism 12A and 12B connects one end of tissue support portion piece 13 to a proximal end of extension portion piece 14A, 14B, respectively. The depicted exemplary sling 10 thus extends between two opposing extension portion distal ends, each optionally including a self-fixating tip 16. Each extension portion is associated with an adjusting mechanism 12A, 12B, which can be actuated intra-operatively to adjust a length of an extension portion.

Still referring to FIG. 1, for use as a single-incision sling for treating urinary incontinence, a total length dimension between ends of the opposing extension portions (e.g., opposing tissue fasteners 16) can be at least sufficient to extend from an obturator internus muscle on one side of the urethra to an obturator internus muscle on the opposite side of the urethra, with tissue support portion piece 13 placed to support tissue of a urethra. For use in treating urinary incontinence by a single incision method, exemplary dimensions of sling 10 may be 6-15 cm in length (between distal ends), e.g., from 6 to 10 or 8 to 10 centimeters in length, and 1-2 cm, more preferably 1-1.5 cm, in width (at the extension portions). These dimensions are for an implant designed to treat incontinence by a single incision method; dimensions can be substantially different for implants designed to treat a different conditions (e.g., fecal incontinence) or for implantation by a different surgical placement method.

In more detail, adjusting mechanisms 12A and 12B each include a line 19, line holder 18, and tether 11A, 11B. Line 19 extends from an end of tissue support piece 13, at which location an end of line 19 is secured (e.g., by a knot, adhesive, thermobonding, or the like). From the fixed end at an end of tissue support portion piece 13, line 19 passes once through aperture 16A of line holder 18, then extends to and loosely through an aperture at end 15 of extension portion piece 14A (or 14B), then extends back to and attaches to line holder 18 at aperture 16B. Tether 11, which is attached at one end to line holder 18 and extends in a proximal direction to tab 20A (or 20B), can be any handling feature that can provide convenient manipulation to provide traction on tether 11A (or 11B), to selectively actuate or place traction on line holder 18 (i.e., body 18D).

Figures 2A, 3A:
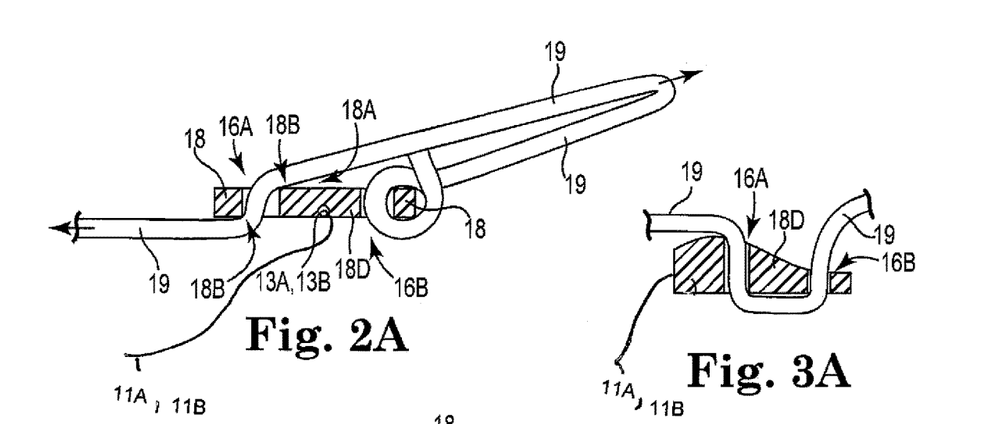
FIG. 2A shows a cross sectional illustration of features of an embodiment of an adjusting mechanism as described.
FIG. 3A shows a cross sectional illustration of features of an embodiment of an adjusting mechanism as described.
Figure 2B:
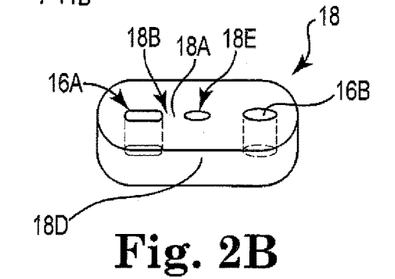
FIG. 2B shows a perspective view of a body of a line holder as described.

FIG. 2B shows additional detail of line holder 18, which includes body 18D, proximal aperture 16A defined by and located at a proximal end of body 18D (the end closest to tissue support portion 13), and distal aperture 16B located at an end of body 18D closest to tissue support portion 13. Optional aperture 18E is at a central location and may be used to attach a tether. Aperture 16A can be of a diameter that allows body 18D to pass along line 19, but that will place friction on line 19 when line 19 is tensioned and contacts internal surfaces of aperture 16A, as well as frictional surfaces 18A and 18B (corners). Aperture 16A can optionally have a dimension (e.g., diameter) in which line 19 fits relatively tightly, e.g., a dimension (e.g., diameter) that is within 25 percent or 10 percent or 1 percent of a dimension (diameter) of line 19; a tight fit can allow relative movement, yet produce a required amount of friction between the inner surface of aperture 16A, and an outer surface of line 19 when line 19 is under tension, optionally deforming body 18D about aperture 16A.

Body 18 can be generally narrow relative to widths of pieces 13, 14A, and 14B. Body 18D also includes one or more friction surfaces 18A (a flat optionally deformable surface) and 18B (corners). Body 18D can be substantially rigid and non-deformable, or may be slightly or substantially deformable upon contact with line 19 placed under tension while passing through aperture 16A and against friction surface 18A. Referring to FIG. 2A line 19 is shown under tension (see arrows); in this state, suture 19 engages friction surfaces 18B (corners), preventing movement of body 18D in a direction toward extension portion piece 14B, in a manner that would remove the tension. Body 18D is not shown to be deformed, but deformation is optional as a result of pressure of tensioned line 19 against one or more of internal surfaces of aperture 16A, corners 18B, and surface 18A, any of which may optionally deform in response to contact with tensioned line 19.

In use, implant 10 is initially placed at a location to support pelvic tissue, with distal ends located at supportive tissue. Line 19 is initially not tensioned. Aperture 16A of adjusting mechanism 18 is loosely engaged about line 19, and body 18D can be moved along a length of line 19. To adjust (reduce) a length of an extension portion, to increase tension of implant 10, and add support to supported pelvic tissue, a user can place traction on one or more of tethers 11A, 11B, by pulling tabs 20A, 20B in a proximal direction. Body 18D is pulled in a proximal direction, which places traction in a proximal direction on the end of line 19 attached at aperture 16B of body 18D. Tension increases along the entire length of line 19, resulting in movement of tissue support portion piece 13 toward extension portion piece 14A, 14B. Continued tension increase results in increased friction between line 19 and body 18B at surfaces 18A and 18B, preventing movement of body 18D relative to line 19 in a direction that would loosen the tension in line 19. Extra lengths of the tethers 11A and 11B can be trimmed upon adjustment.

Optionally and preferably an implant (e.g., any embodiment described herein) can include two adjusting mechanisms at opposing locations of an implant. The two adjusting mechanisms can be actuated in coordination, meaning that the tension or length of both of the two opposing extension portions are adjusted together. Such coordinated use of two adjusting mechanisms can advantageously allow a surgeon or other user to adjust the placement, length, or tension of an implant or extension portion in a manner that does not cause a urethra or other tissue to become located at a non-anatomical position relative to a midline of the patient. Stated differently, two opposing adjusting mechanisms can be actuated and adjusted together to prevent the urethra or other supported tissue from being moved in a left or a right direction within the patient, which will maintain a correct anatomical position of the urethra or other supported tissue, e.g., at a midline of the patient.

Figure 3B:
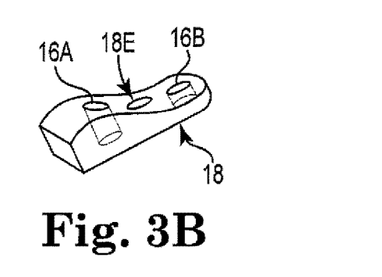
FIG. 3B shows a perspective view of a body of a line holder as described.

FIGS. 3A and 3B are side cross-section and side perspective views, respectively, of an alternate body 18D. Body 18D includes an aperture 16A that is relatively longer (relative to aperture 16A of FIGS. 2A and 2B), traversing a proximal end of body 18D that is relatively thicker. In use, the relatively longer aperture 16A can produce greater friction and improved holding power between line 19 and the inner surface of aperture 16A.

Figure 4:
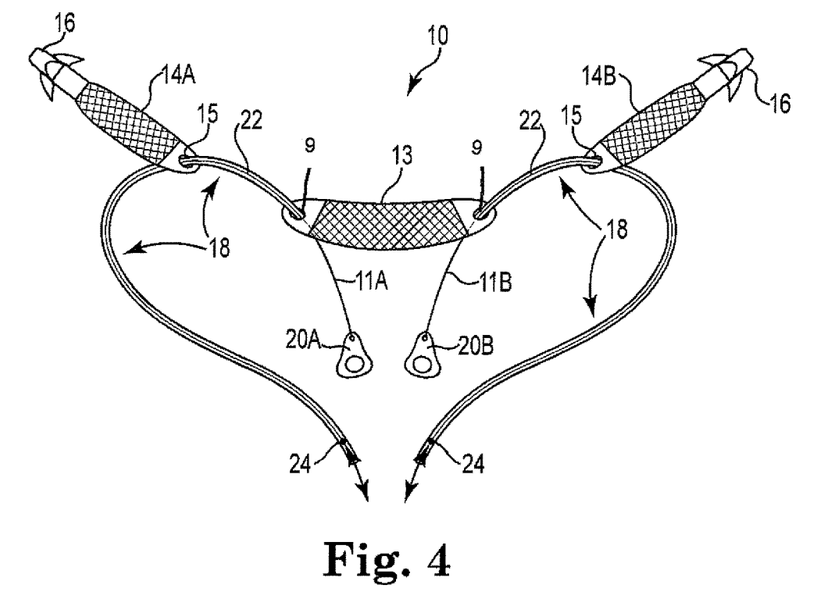
FIGS. 4 and 5 show an embodiment of an implant as described.
Figure 5:
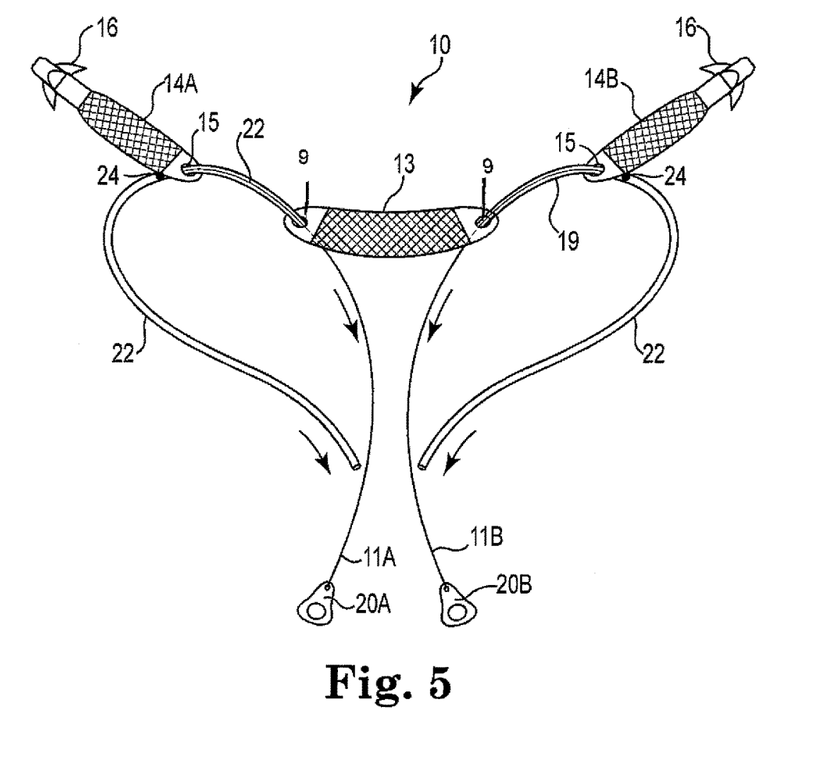

FIGS. 4 and 5 illustrate an alternative embodiment of a three-piece implant 10 that includes features similar to implant 10 of FIGS. 1 and 2, but with alternate adjusting mechanisms 18, including a line and a line holder. Referring to FIGS. 4 and 5, each adjusting mechanism 18 includes a two-piece combination of line (tubing) 22 and line holder (e.g., locking ball or other stopping mechanism) 24. Each line (tubing) 22 can be, e.g., a flexible mesh, fabric, or polymeric tubing, e.g., thin-walled polypropylene, fabric, woven tubing, or the like. One end of line 22 is attached securely to an end of tissue support portion piece 13. Line 22 extends from the end of tissue support portion piece 13, toward and through aperture 15 of extension portion piece 14A, 14B, then in a proximal direction. Tether 11A, 11B can be a cord or suture that fits and is placed within the interior of tubing 22, and that includes line holder 24—moveable within tubing 22—at an end opposite tab 20A, 20B, at a location distal to aperture 15. (In alternate embodiments, a modification of the illustrated embodiment, one end of line 22 is attached securely to an end of extension portion piece 13 at aperture 15. In this embodiment, line 22 extends from aperture 15 at the proximal end of extension portion piece 13, toward and loosely through aperture 9 at the end of tissue support portion piece 13, then beyond in a proximal direction. Line holder 24 and tether 11A, 11B, function in the same manner described.)

Line holder 24 may be made of any material identified herein for a line holder, such as a polymeric material that may be elastomeric and deformable, or rigid and not substantially deformable upon contact with a line (tubing 22) in tension; examples of materials include polymeric materials including polyolefins materials (e.g., polypropylene), elastomeric materials (e.g., silicone, polyurethane, and the like), and metal materials. The size and shape of the line holder can be suitable to fit and move within tubing 22, and may be cylindrical, spherical, cubic, conical, spiral, etc. Line holder 24 has a dimension (e.g., diameter) that is larger than a diameter of aperture 15. The dimension may be smaller than a non-deformed dimension of tubing 22, if tubing 22 is deformable to accommodate the larger dimension of the line holder. Line holder 24 can be moved along a length of tubing 22, optionally with deformation of tubing 22, but may be held frictionally when tension is placed along tubing 22, with line 22 under tension. Pulling tethers 11A and 11B cause line holder 24 to move along a length of line (tubing) 22 toward aperture 15, whereupon line holder 24 remains in place frictionally within tubing 22. With line 22 under tension, extension portion piece 14A, 14B is prevented from moving away from tissue support portion piece 12, based on the presence of line holder 24 in tubing 22, adjacent to aperture 15. Tethers 11A and 11B, and both lines (tubing) 22 can be trimmed as desired, after final adjustment.

In use, implant 10 is initially placed at a location to support pelvic tissue, with distal ends located at supportive tissue. Each of opposing lines 22 is initially not tensioned. Each line 22 is attached at one end to an end of tissue support portion piece, and passes loosely through an aperture 15 of extension portion piece 14A or 14B. To adjust (reduce) a length of an extension portion, to increase tension of implant 10, and add support to the pelvic tissue, a user can place traction in a proximal direction (see arrows at FIG. 5) on one or more of a proximal end of line 22. Once desired positioning of pelvic tissue and tension of implant 10 are achieved, line holders 24 can be brought into place within each tube 22, behind each aperture 15, by pulling tabs 20A and 20B in a proximal direction (see arrows at FIG. 5). Each line holder 24 is brought into place behind an aperture 15. A dimension of line holder 24 that is larger than a dimension of aperture 15 prevents aperture 15 from passing over line holder 24 within tube 22, thus maintaining a (maximum) length of implant 10 and preventing movement of tissue support portion piece 13 in a direction away from each of extension portions 14A and 14B, in a manner that would loosen the tension in line 19 or diminish the support provided to the supported pelvic tissue. Extra lengths of the tethers 11A, 11B and each tubing 22 can be trimmed upon adjustment.

Figure 6:
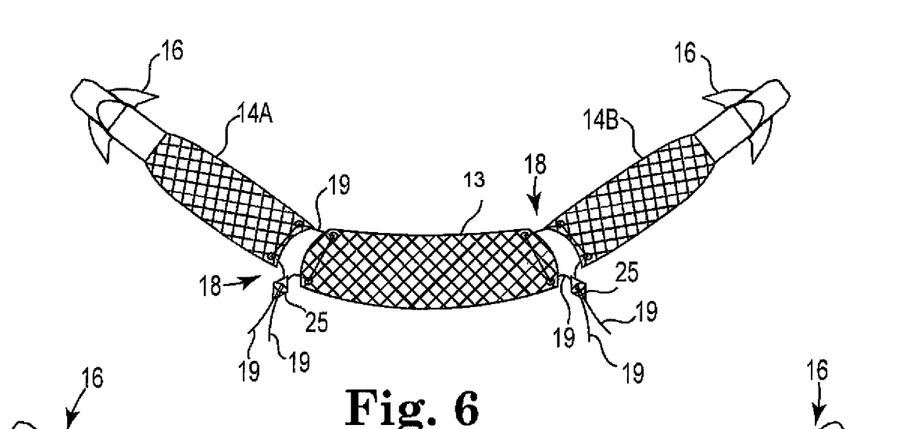
FIGS. 6 and 7 show an embodiment of an implant as described.
Figure 7:
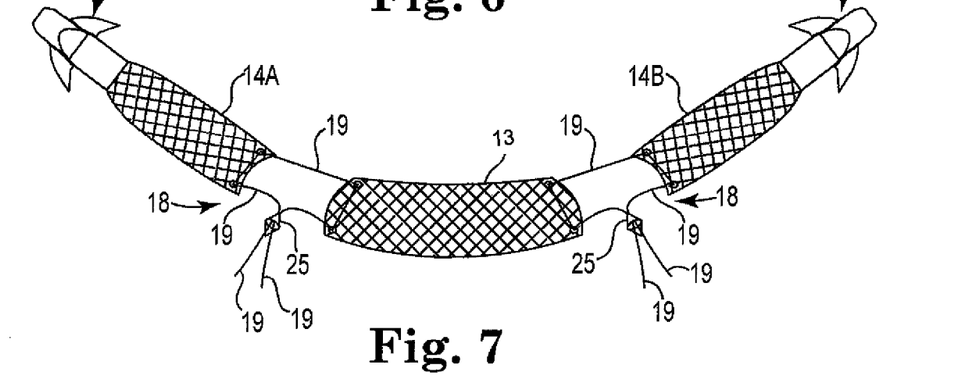

FIGS. 6 and 7 illustrate an alternative embodiment of a three-piece implant 10 that includes features similar to implant 10 of FIGS. 1 and 2, but with alternate adjusting mechanisms 18. Referring to FIGS. 6 and 7, each implant adjusting mechanism 18 includes a two-piece combination of line (e.g., suture) 19 and line holder 25. Each line 19 can be, e.g., a flexible suture, cord, wire, tie (e.g., pull tie, with ratcheting or frictional surfaces) or fiber, which may be natural or synthetic (e.g., polymeric). Each line 19 connects extension portion piece 14A, 14B to an end of tissue support portion piece 13 by a loop that passes loosely through adjacent ends of each piece, then extends proximally as two loose ends (tethers). Pulling loose ends 19 in a proximal direction will cause a distance between extension portion piece 14A, 14B, and tissue support portion piece 13 to be decreased. FIG. 6 shows the extension portions at reduced length relative to the lengths of the extension portions shown at FIG. 7.

Each adjusting mechanism 18 includes a line holder 25 that is moveably attached to both loose ends of sutures 19. Line holder 25 can be any type of device, such as a collar, grommet, slide, etc., that frictionally attaches to the two loose suture ends, and can engage the two loose suture ends in a manner that does not allow post-operative movement of line holder 25 relative to line 19. Examples of line holders 25 can include silicone compression locks, tab connectors, pull-tie connectors, or other selective ratcheting or locking mechanisms made, for example, of a polymer or an elastomer that frictionally engages line 19 with sufficient force to maintain a desired tension on an implant or extension portion, without undue post-operative movement of line 19 relative to line holder 25.

Figure 8:
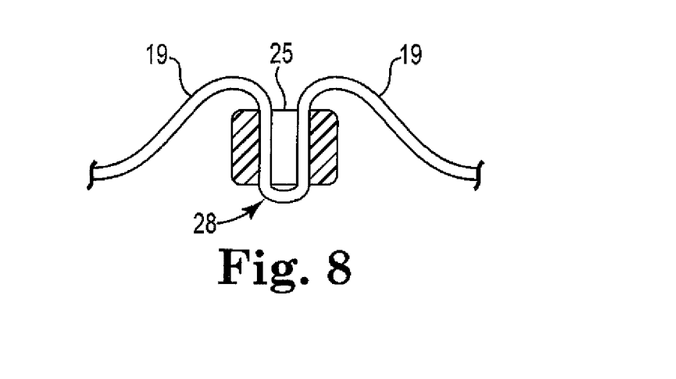
FIG. 8 shows a perspective view of a line holder as described.

FIG. 8 shows a cross sectional view of line holder 25 in the form of an elastomeric collar that includes an aperture 25A dimensioned to receive two lines 19, as illustrated. Aperture 25A can optionally have a dimension (e.g., diameter) in which two lines 19 fit relatively tightly, e.g., a dimension (e.g., diameter) that is within 25 percent or 10, 5, or 1 percent of a dimension (diameter) line 19; a tight fit can produce a required amount of friction between the inner surface of aperture 25A and an outer surface of line 19, especially with tension on line 19, to prevent post-operative movement between lines 19 and line holder 25.

Figure 9:
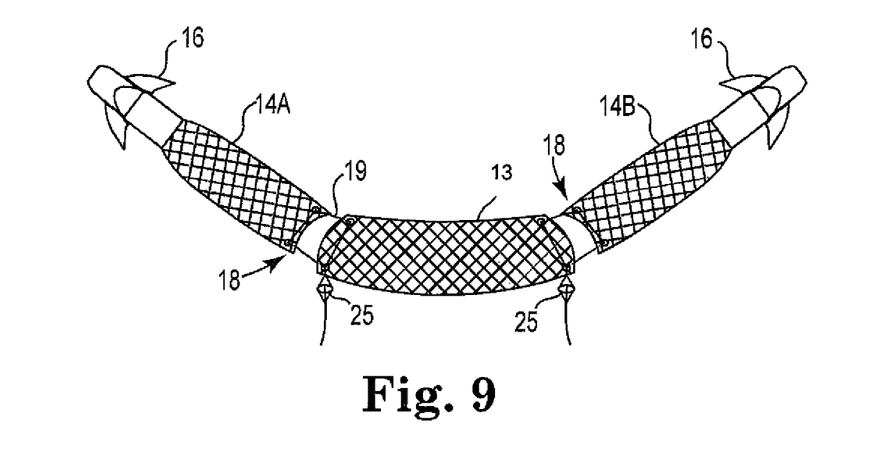
FIGS. 9 and 10 show an embodiment of an implant as described.
Figure 10:
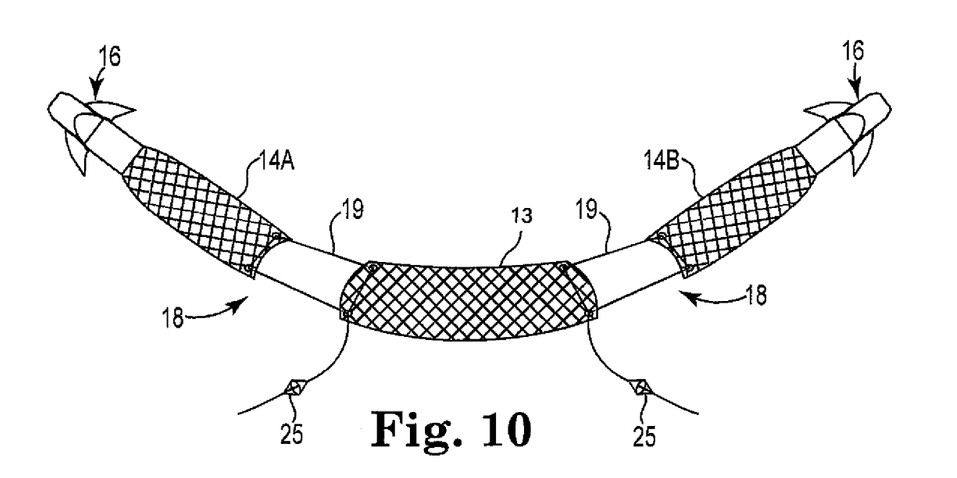
Figures 11A, 11B:
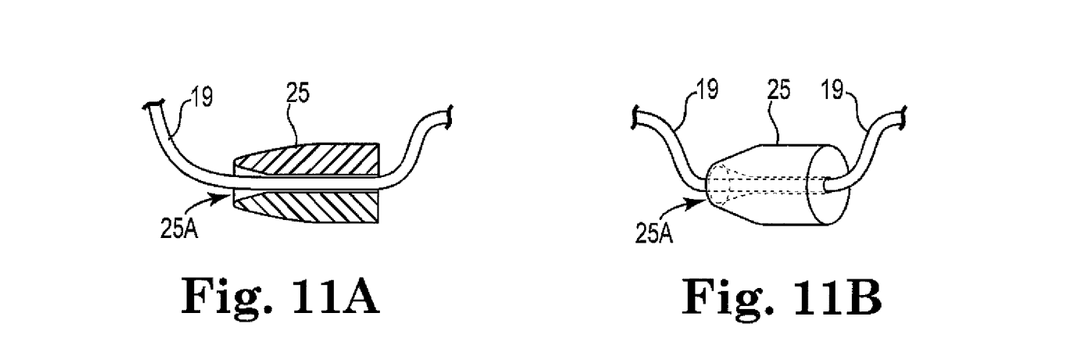
FIGS. 11A, 11B, 11C, and 11D show cross section and perspective views of embodiments of line holders as described.
All figures are not to scale.
Figures 11C, 11D:
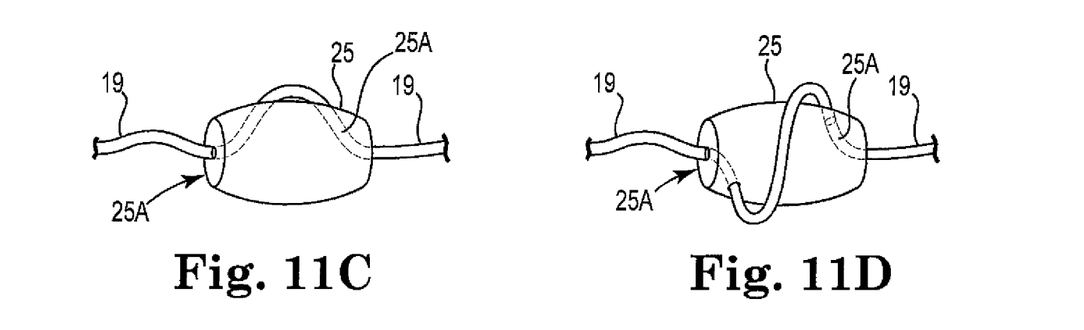

FIGS. 9 and 10 illustrate an alternative embodiment of a three-piece implant 10 that includes features similar to implant 10 of FIGS. 6 and 7, but with alternate adjusting mechanisms 18. Referring to FIGS. 9 and 10, each implant adjusting mechanism 18 includes a two-piece combination of line (e.g., suture) 19 and line holder 25. Each line 19 can be, e.g., a flexible suture, cord, tie (e.g., pull-tie with frictional surfaces) wire, or fiber, which may be natural or synthetic (e.g., polymeric). One end of line 19 is attached securely to an end of tissue support portion piece 13 (alternately, to an end of an extension portion piece 14A or 14B). Each line 19 connects an extension portion piece 14A or 14B to an end of tissue support portion piece 13 by a loop that ends at one loose end (tether) 19 extending away from implant 10. Pulling loose end 19 in a proximal direction will cause a distance between extension portion piece 14A, 14B, and tissue support portion piece 13, to be decreased.

FIGS. 11A, 11B, 11C, and 11D show cross sectional (FIG. 11A) and side or side-perspective views (FIGS. 11B, 11C, and 11D) of alternate line holders 25 in the form of an elastomeric collar or slide that includes one or multiple apertures 25A dimensioned to receive a single lines 19, as illustrated. Each aperture or combination of apertures 25A of a line holder can optionally have a dimension (e.g., diameter) in which a single line 19 fits relatively tightly, e.g., a dimension (e.g., diameter) that is within 25 percent or 10, 5, or 1 percent of a dimension (diameter) line 19; a tight fit can produce a required amount of friction between the inner surface of aperture 25A and an outer surface of line 19, to prevent post-operative movement between line 19 and line holder 25.

In use, implant 10 of FIGS. 6 through 11 is initially placed at a location to support pelvic tissue, with distal ends located at supportive tissue. Each of opposing lines 19 is initially not tensioned. To adjust (reduce) a length of an extension portion to increase tension of implant 10 and add support to the pelvic tissue, a user can place traction in a proximal direction on one or more of lines 19. Once desired positioning of pelvic tissue and tension of implant 10 are achieved, line holders 25 can be brought into place against implant 10, preventing movement of tissue support portion piece 13 in a direction away from each of extension portions 14A and 14B, in a manner that would loosen the tension in line 19 or diminish the support provided to the supported pelvic tissue. Extra lengths of the lines 19 on a proximal side of a holder 25 can be trimmed upon adjustment.

Generally, an implant as described can be initially placed with approximate positioning and effect (e.g., supportive force, approximation, tension, etc.) to support selected pelvic tissue. Subsequently, lengths of opposing extension portions can be adjusted by use of adjusting mechanisms 18. Each self-fixating tip 16 can be placed within supportive tissue such as tissues of a patient's two opposing obturator foramen while the tissue support portion of the implant supports a urethra, bladder neck, vaginal tissue, etc.

With reference to a transvaginal method of treating urinary incontinence, exemplary method steps include an initial step of placing implant 10, followed by an adjustment step for adjusting one or two lengths of the extension portions, via adjusting mechanisms 18. In a first step, a self-fixating tip 16 can be placed at an end of an insertion tool (optionally including a release mechanism), passed through a medial incision in a patient (e.g., transvaginally), and placed securely into tissue of an obturator foramen. A second self-fixating tip 16 located on the opposite extension portion of implant 10 can be inserted into tissue of the opposite obturator foramen using the same insertion tool or a second identical or similar tool. Optionally, each step of placing a self-fixating tip at tissue of an obturator foramen can include the use of a release mechanism capable of engaging a self-fixating tip 16 at a tip of the insertion tool shaft, placing the self-fixating tip 16 at supportive tissue, releasing self-fixating tip 16 in the supportive tissue, and withdrawing the insertion tool from the patient.

With opposing self-fixating tips installed at opposing obturator foramen, the tissue support portion (of piece 13) is located below a urethra, to support the urethra. The surgeon can assess the position, tension, or both, of implant 10 supporting the urethra, and whether a length of one or two extension portions, should be adjusted. Optionally the surgeon may use a "cough test," by asking the patient to cough and checking efficacy of the treatment. If adjustment is necessary, the surgeon can actuate an adjusting mechanism 18, e.g., by pulling a tether or line, to reduce a length of an extension portion, i.e., a distance between extension portion piece 14A or 14B and tissue support portion piece 13.

In preferred embodiments, the two adjusting mechanisms 18 can be used in coordination, meaning that the tension or length of both of the two opposing extension portions are adjusted in a coordinated manner (e.g., simultaneously or non-simultaneously but alternately and in succession). Such coordinated use of two adjusting mechanisms 18 advantageously allow the surgeon to adjust the placement, length, or tension of implant 10 in a manner that does not cause the urethra (or other supported tissue) to become located at a non-anatomical position relative to a midline of the patient. Stated differently, opposing adjusting mechanisms 18 can be adjusted together (optionally but not necessarily simultaneously using two adjusting tools) to prevent the urethra or other supported tissue from being moved in a left or a right direction within the patient, which will maintain a correct anatomical position of the urethra or other supported tissue, e.g., at a midline of the patient.

The disclosed systems, their various components, structures, features, materials and methods may have a number of suitable configurations as shown and described in the previously-incorporated references. Various methods and tools for introducing, deploying, anchoring and manipulate device, implants, and the like as disclosed in the previously-incorporated references are envisioned for use with the present invention as well.

All patents, patent applications, and publications cited herein are hereby incorporated by reference in their entirety as if individually incorporated, and include those references incorporated within the identified patents, patent applications and publications.

The invention claimed is:

1. A pelvic implant useful to treat a pelvic condition, the implant comprising:
    a tissue support portion, a first extension portion, and a second extension portion,
    a first adjusting mechanism comprising:
    a first line at the first extension portion, the first line extending between the tissue support portion and the first extension portion, the first line configured to be tightened to adjust a length of the first extension portion,
    a first line holder that engages the first line at a location between the tissue support portion and the first extension portion, the first line holder configured to maintain an adjusted length of the first extension portion,
    a first tab,
    a first tether having a first end portion and a second end portion, the first end portion of the first tether being securely attached to the first line holder, the second end portion of the first tether being coupled to the first tab, wherein pulling the first tab which is configured to move the first line holder along the first line in a direction toward the tissue support portion reduces a first distance between the first extension portion and the tissue support portion,
    a second adjusting mechanism comprising:
    a second line at the second extension portion, the second line configured to be tightened to adjust a length of the second extension portion,
    a second line holder that engages the second line at a location between the tissue support portion and the second extension portion, the second line holder is configured to maintain an adjusted length of the second extension portion, a first self-fixating tip disposed at a distal end of the first extension portion, and a second self-fixating tip disposed at a distal end of the second extension portion.

2. The implant as recited at claim 1, comprising:
a tissue support portion piece comprising the tissue support portion, a first end, and a second end,
a first extension portion piece comprising the first extension portion, a proximal end, and the distal end of the first extension portion,
a second extension portion piece comprising the second extension portion, a proximal end, and the distal end of the second extension portion,
wherein the first line connects the proximal end of the first extension portion piece and the first end of the tissue support portion piece, and
the second line connects the proximal end of the second extension portion piece and the second end of the tissue support portion piece.

3. The implant as recited at claim 1, wherein the implant has a length to allow the first and second self-fixating tips to be placed at tissue of opposing obturator foramen of a patient, with the tissue support portion supporting tissue of a urethra or an anus.

4. The implant as recited at claim 1, wherein the first line is coupled to a first end of the tissue support portion, the first line extending through the first line holder and through an aperture at a proximal end of the first extension portion, the first line being coupled to the first line holder.

5. The implant as recited at claim 1, wherein, with the first line under tension, the first line holder is configured to prevent the distance between the first extension portion and the tissue support portion from increasing.

6. The implant as recited at claim 1,
wherein the first line is coupled to a first end of the tissue support portion, the first line extending through the first line holder and through an aperture at a proximal end of the first extension portion, the first line being coupled to the first line holder, and
wherein the second line is coupled to a second end of the tissue support portion, the second line extending through the second line holder and through an aperture at a proximal end of the second extension portion, the second line being coupled to the second line holder.

7. The implant as recited at claim 1, further comprising a second tab, and a second tether having a first end portion and a second end portion, the first end portion of the second tether securely coupled to the second line holder, the second end portion of the second tether being coupled to the second tab.

8. The implant as recited at claim 7, wherein pulling the second tab is configured to move the second line holder along the second line in a direction toward the tissue support portion to reduce a second distance between the second extension portion and the tissue support portion.

9. The implant as recited at claim 8, wherein, with the second line under tension, the second line holder is configured to prevent the second distance from increasing.

10. The implant as recited at claim 1, wherein, with the implant placed within a patient with the first and second self-fixating tips at tissue of opposing obturator foramen and the tissue support portion supporting tissue of a urethra or an anus, each of the first tether and the second tether is configured to be accessed through a medial incision of the patient to actuate each of the first and second adjusting mechanisms.

11. The implant as recited at claim 1, wherein
the first line comprises a flexible tube that is coupled to a first end of the tissue support portion and the flexible tube extends through an aperture at a proximal end of the first extension portion,
the first adjusting mechanism comprises an elongate member, the elongate member moveably extending through the flexible tube, the first line holder being secured to a distal end of the elongate member, the first line holder having a dimension larger than the aperture,
pulling the first line reduces the first distance between the first extension portion and the tissue support portion, and
pulling the elongate member causes the first line holder to engage the aperture to prevent the first distance from increasing.

12. The implant as recited at claim 1, wherein the first line holder comprises an elastomeric body configured to be deformed upon contact with the first line under tension.

13. A method of treating a pelvic condition, the method comprising:
providing the implant as recited at claim 1,
placing the implant in a patient to support pelvic tissue,
actuating the first adjusting mechanism to adjust the length of the first extension portion.

14. The method as recited at claim 13, further comprising actuating the second adjusting mechanism to adjust the length of the second extension portion.

15. The method as recited at claim 13, wherein the pelvic condition is selected from the group consisting of: fecal incontinence and urinary incontinence.

16. The method as recited at claim 13 for treating urinary incontinence, the method comprising:
creating a medial incision in the patient,
placing the tissue support portion to contact tissue to support the urethra,
placing a distal end of the first extension portion in a tissue path extending toward a first obturator foramen of the patient, and
placing a distal end of the second extension portion in a tissue path extending toward a second obturator foramen of the patient.

* * * * *